United States Patent
Ryu

(10) Patent No.: US 7,838,710 B2
(45) Date of Patent: Nov. 23, 2010

(54) SELECTIVE HYDROGENATION PROCESS AND CATALYST

(75) Inventor: J. Yong Ryu, Pasadena, TX (US)

(73) Assignee: Catalytic Distillation Technologies, Pasadena, TX (US)

(*) Notice: Subject to any disclaimer, the term of this patent is extended or adjusted under 35 U.S.C. 154(b) by 0 days.

(21) Appl. No.: 12/539,229

(22) Filed: Aug. 11, 2009

(65) Prior Publication Data

US 2009/0299114 A1    Dec. 3, 2009

Related U.S. Application Data

(62) Division of application No. 10/969,613, filed on Oct. 20, 2004.

(51) Int. Cl.
  *C07C 5/05* (2006.01)
  *B01J 23/00* (2006.01)
  *B01J 21/00* (2006.01)
  *B01J 20/00* (2006.01)
  *B01J 29/00* (2006.01)

(52) U.S. Cl. ............ 585/274; 502/327; 502/328; 502/330; 502/331; 502/332; 502/333; 502/339; 502/341; 502/346; 502/348; 502/355; 502/415; 502/439

(58) Field of Classification Search ............ 585/260, 585/274; 502/327, 328, 330, 331, 332, 333, 502/339, 341, 346, 348, 355, 415, 439
See application file for complete search history.

(56) References Cited

U.S. PATENT DOCUMENTS

| | | | |
|---|---|---|---|
| 2,620,314 A | 12/1952 | Hoekstra et al. | |
| 3,076,858 A | 2/1963 | Frevel et al. | |
| 3,471,583 A | 10/1969 | Fleming et al. | |
| 3,641,182 A | 2/1972 | Box, Jr. et al. | |
| 3,679,763 A * | 7/1972 | Livingston | 585/262 |
| 3,751,508 A | 8/1973 | Fujiso et al. | |
| 3,793,388 A | 2/1974 | Pitzer et al. | |
| 3,883,444 A | 5/1975 | Maselli et al. | |
| 4,169,815 A | 10/1979 | Drehman | |
| 4,172,810 A | 10/1979 | Mitchell, III et al. | |
| 4,179,408 A | 12/1979 | Sanchez et al. | |
| 4,261,862 A * | 4/1981 | Kinoshita et al. | 502/304 |
| 4,263,020 A * | 4/1981 | Eberly, Jr. | 95/136 |
| 4,273,735 A | 6/1981 | Jacques et al. | |
| 4,274,981 A * | 6/1981 | Suzuki et al. | 502/178 |
| 4,425,312 A * | 1/1984 | Brignac | 423/230 |
| 4,440,956 A | 4/1984 | Couvillion | |
| 4,581,343 A | 4/1986 | Blanchard et al. | |
| 4,690,806 A * | 9/1987 | Schorfheide | 423/230 |
| 5,028,665 A | 7/1991 | Hucul | |
| 5,258,340 A | 11/1993 | Augustine et al. | |
| 5,352,337 A * | 10/1994 | Kobayashi et al. | 205/617 |
| 5,756,420 A | 5/1998 | Wittenbrink et al. | |
| 5,767,040 A | 6/1998 | Bhattacharyya et al. | |
| 5,866,734 A | 2/1999 | Flick et al. | |
| 6,127,310 A | 10/2000 | Brown et al. | |
| 6,218,326 B1 | 4/2001 | Datta et al. | |
| 6,350,717 B1 | 2/2002 | Frenzel et al. | |
| 6,388,150 B1 | 5/2002 | Overbeek et al. | |
| 6,417,419 B1 | 7/2002 | Abrevaya et al. | |
| 6,437,206 B1 | 8/2002 | Meyer et al. | |
| 6,509,292 B1 | 1/2003 | Blankenship et al. | |
| 6,576,588 B2 | 6/2003 | Ryu et al. | |
| 6,607,678 B2 | 8/2003 | Wang et al. | |
| 6,627,578 B2 | 9/2003 | Xu et al. | |
| 6,638,599 B2 * | 10/2003 | Masaki et al. | 428/141 |
| 6,794,552 B2 | 9/2004 | Cheung et al. | |
| 6,846,471 B2 * | 1/2005 | Hotta et al. | 423/239.1 |
| 6,903,046 B2 | 6/2005 | Ding | |
| 6,958,310 B2 | 10/2005 | Wang et al. | |
| 7,022,645 B2 | 4/2006 | Ryu et al. | |
| 7,196,035 B2 | 3/2007 | Ryu et al. | |

(Continued)

FOREIGN PATENT DOCUMENTS

EP    1090900 B1    4/2001

(Continued)

OTHER PUBLICATIONS

Australian Patent Office Search Report and First Written Opinion, dated Jul. 21, 2008, 32 pages.

(Continued)

*Primary Examiner*—Cam N Nguyen
(74) *Attorney, Agent, or Firm*—Osha • Liang LLP

(57) ABSTRACT

A supported catalyst for selective hydrogenation of acetylenes comprising 3-15 wt. % Ni promoted with 0.005-0.2 Pd on a support. The catalyst is prepared by depositing nickel promoted with palladium on a support, containing one or more optional elements from copper, silver, Group IA (Li, Na, K, Rb, Cs, Fr) and Group IIA (Be, Mg, Ca, Sr, Ba, Ra) and B (Zn, Cd,) of the periodic table of elements and characterized as:

| Component | Range of component | Preferably |
|---|---|---|
| | wt. % | wt. % |
| Ni | 3-15 | 4-11 |
| Cu | 0-1 | 0.0-0.6 |
| Pd | 0.005-0.2 | 0.01-0.1 |
| Ag | 0-10 | 0-5 |
| Group IA | 0-2.5 | 0-1.5 |
| Group IIA & B | 0-25 | 0.1-5. |

20 Claims, No Drawings

U.S. PATENT DOCUMENTS

| | | |
|---|---|---|
| 2003/0171629 A1 | 9/2003 | Ryu et al. |
| 2004/0176651 A1 | 9/2004 | Molinier et al. |
| 2005/0033099 A1 | 2/2005 | Ryu et al. |
| 2005/0048658 A1 | 3/2005 | Johnson et al. |
| 2005/0096217 A1 | 5/2005 | Rokicki et al. |
| 2005/0203320 A1 | 9/2005 | Ryu |
| 2005/0209491 A1 | 9/2005 | Ryu |
| 2005/0272964 A1 | 12/2005 | Ryu et al. |
| 2006/0030482 A1 | 2/2006 | Ryu et al. |
| 2008/0119354 A1 | 5/2008 | Ryu |

FOREIGN PATENT DOCUMENTS

| | | |
|---|---|---|
| WO | 9955648 A1 | 11/1999 |
| WO | 2006/044005 A2 | 4/2006 |

OTHER PUBLICATIONS

English Patent Abstract of Japanese Publication, Yamamoto et al, Development of High-Performance Automotive Three-Way Palladium Catalyst Using Nickel Aluminate Support, Nippon Kagaku Kaishi, 2000, vol. 8, pp. 553-560.

PCT International Search Report issued in PCT Application No. PCT/US2005/25606 dated Apr. 11, 2008 (2 pages).

PCT Written Opinion issued in PCT Application No. PCT/US2005/25606 dated Apr. 7, 2008 (3 pages).

International Preliminary Report on Patentability issued in PCT Application No. US2005/025606 dated Mar. 19, 2009. (5 pages).

Handbook of Commercial Catalysts, pp. 105-138, Howard F. Rase, CRC Press, 2000.

US Office Action issued in U.S. Appl. No. 10/969,613 dated Apr. 28, 2009 (12 pages).

US Office Action issued in U.S. Appl. No. 10/969,613 dated Dec. 10, 2008 (8 pages).

US Office Action issued in U.S. Appl. No. 10/969,613 dated Aug. 26, 2008 (3 pages).

US Office Action issued in U.S. Appl. No. 10/969,613 dated Apr. 21, 2008 (11 pages).

US Office Action issued in U.S. Appl. No. 10/969,613 dated Jan. 11, 2008 (5 pages).

U.S. Office Action issued in U.S. Appl. No. 10/969,613 dated Feb. 17, 2010 (9 pages).

US Office Action issued in U.S. Appl. No. 12/539,229 dated May 17, 2010 (8 pages).

Substantive Examination Report and Search Report issued Jul. 15, 2010 by the Intellectual Porperty Corporation of Malaysia in corresponding Malaysian patent application No. PI20053596 (3 pages).

US Office Action issued in U.S. Appl. No. 10/969,613 dated Jul. 28, 2010 (8 pages).

* cited by examiner

SELECTIVE HYDROGENATION PROCESS AND CATALYST

CROSS-REFERENCE TO RELATED APPLICATION

This application, pursuant to 35 U.S.C. §120, claims benefit to U.S. patent application Ser. No. 10/969,613 filed Oct. 20, 2004. That application is incorporated by reference in its entirety.

BACKGROUND OF THE INVENTION

1. Field of the Invention

The present invention relates to the selective removal of acetylenic compounds from hydrocarbon streams using specific Ni-based catalysts and the process of making the catalysts. The process is particularly useful in cleaning up MAPD (methyl acetylene and propadiene) and acetylene in crude mixed olefin streams or phenylacetylene in crude styrene streams by selective hydrogenation in the presence of the Ni-based catalyst.

2. Related Information

Acetylenic impurities such as acetylene, methyl acetylene, vinyl acetylene, ethyl acetylene, and 2-methyl-1-buten-3-yne are found in various crude mixed $C_2$-$C_5$ streams, for example in the manufacture of olefins such as ethylene, propylene, butadiene and isoprene. These acetylenic impurities need to be removed with a minimum loss of the useful olefinic materials, i.e., ethylene, propylene, butenes, butadiene, isoprene and the like.

For example, 1,3-butadiene is an important raw material used to produce various polymers such as butadiene-styrene copolymer. One of the processes for producing 1,3-butadiene is co-production of various olefins by steam cracking of petroleum fractions. The crude mixed $C_4$ stream from a steam cracker is selectively hydrogenated to partially remove $C_4$ acetylenic compounds. The selectively hydrogenated stream is sent to the 1,3-butadiene recovery unit where solvent extractive distillation techniques are used to separate 1,3-butadiene from the rest of components in the mixed stream. Solvent extractive distillation is expensive to operate and energy consumption is intensive.

Complete removal of $C_4$ acetylenic compounds in the stream with high recovery of 1,3-butadiene is highly desirable to reduce the production cost of 1,3-butadiene and produce a premium quality product for polymer production. However, formerly it was technically impossible to completely remove $C_4$ acetylenes in crude mixed streams by selective hydrogenation without unacceptably high loss of 1,3-butadiene due to over-hydrogenation of 1,3-butadiene. Therefore, an improved inexpensive process via a highly active and selective catalyst is highly desirable to produce premium quality 1,3-butadiene without paying a penalty for high loss of 1,3-butadiene due to over-hydrogenation.

The preferred technique for the purification in commercial practice is the selective hydrogenation of acetylenic compounds over hydrogenation catalysts. Supported Pd, Ni, Cu and Co catalysts are known as useful for the hydrogenation of acetylenes (Handbook of Commercial Catalysts, pp. 105-138, Howard F. Rase, CRC Press, 2000). The most preferred catalysts in prior commercial applications of selective hydrogenation of acetylenes are palladium-based catalysts such as Pd, Pd/Pb, Pd/Ag or Pd/Au on a support such as alumina and the copper catalysts on a support such as alumina. Pd catalysts were the most preferred catalysts because of high activity and higher selectivity compared with other known metal catalysts.

However, palladium-based catalysts are not selective enough to completely remove $C_4$ acetylenes without an unacceptable amount of 1,3-butadiene loss due to over-hydrogenation. Another inherent problem of palladium-based catalysts is the loss and migration of palladium due to the formation of soluble Pd complex compounds by the reaction of Pd atoms on the catalyst surface with vinyl acetylene, if the hydrogenation is carried out with a liquid phase. Silver and gold have been used to minimize the loss of palladium and reduce catalytic polymerization of acetylenic compounds.

The copper-based catalysts are very selective so that the recovery of 1,3-butadiene from the mixed stream is very high compared with palladium-base catalysts. The activity of copper catalysts is very low compared with palladium-based catalysts, and a large volume of catalyst and large reactor are required. Also because the deposition of heavy carbonaceous materials on the catalyst occurs quickly, frequent regeneration of catalysts necessitates multiple reactors.

Ni catalysts in any form are very active catalysts for selective hydrogenation of acetylenes and dienes. According to R. S. Mann et al. (Can. J. Chem. 46, p. 623, 1968), Ni and Ni—Cu alloy catalysts are effective for methyl acetylene hydrogenation. The catalytic activity rapidly increases with addition of copper to nickel up to 25 wt. % in alloy catalyst. The selectivity to propylene and extent of polymerization increase with the increase of copper in the alloy. Nickel-based catalysts have been used in commercial processes for the selective hydrogenation of acetylenic impurities in mixed steams of olefins and diolefins.

Despite recent improvements made in the performance of catalysts, still further improvement is desired for the selective hydrogenation of acetylenic compounds in a $C_2$ or $C_3$ mixed olefin stream to improve selectivity, activity and catalyst cycle time for the production of large volume olefins such as propylene and ethylene. For the commercial production of large volume commodities, such as propylene, even small improvements in selectivity of MAPD to propylene or catalyst activity is highly desirable.

SUMMARY OF THE INVENTION

Briefly the present catalyst is a supported catalyst for selective hydrogenation of acetylenes comprising Ni deposited with a promoting amount of Pd on an aluminum oxide support, which contains mixed oxides of $MAl_2O_4$ with spinel structures, where M is any divalent cation, preferably comprising 3-15 wt. % Ni promoted with 0.005-0.2 Pd on a support. The catalysts are prepared by depositing nickel promoted with palladium on a support, containing one or more optional elements from copper, silver, Group IA (Li, Na, K, Rb, Cs, Fr) and Group IIA (Be, Mg, Ca, Sr, Ba, Ra) and B (Zn, Cd) of the periodic table of elements and characterized as:

| Component | Range of component wt. % | Preferably wt. % |
|---|---|---|
| Ni | 3-15 | 4-11 |
| Cu | 0-1 | 0.01-0.6 |
| Pd | 0.005-0.2 | 0.01-0.1 |
| Ag | 0-10 | 0-5 |
| Group IA | 0-2.5 | 0-1.5 |
| Group IIA & B | 0-25 | 0.1-5 |

Where the weight % of the active components are based on the total weight of active components and support.

A promoting amount of Pd means an amount less than 10% of the Ni present.

DETAILED DESCRIPTION

The catalysts are useful for hydrogenation reactions such as selective hydrogenation to remove acetylenic impurities in various mixed streams of $C_2$-$C_{12}$ olefins, diolefins and styrene, and hydrogenation of benzene to cyclohexane. Passing a mixture of a hydrocarbon feed stream and hydrogen gas through a catalytic reaction zone or a series of two catalytic reaction zones which carries out hydrogenation reactions such as the selective hydrogenation of acetylenic compounds. A catalytic reaction zone may contain one catalyst or several different catalysts. If the selective hydrogenation is carried out in a series of two catalytic reaction zones, optionally the catalyst in the second reaction zone may contain Cu as a promoter and modifier. The poisoning effects of organic mercaptans and organo-mercuric compounds for the nickel catalysts promoted with Cu in the second catalytic reaction zone are neutralized in the first catalytic reaction zone. A portion of the catalyst in the first catalytic reaction zone is sacrificed as a guard bed for the poisonous impurities. The improvement made for the hydrogenation process in this invention is higher selectivity or higher recovery of the useful materials such as mono-olefins, diolefins, or both, than those processes based on conventional nickel catalysts or conventional palladium-based catalysts. The $C_4$ acetylenic impurities in a mixed crude butadiene stream can be completely removed by selective hydrogenation with higher recovery of 1,3-butadiene in the present process, than prior art nickel catalysts. Therefore, this invention allows elimination of one of two extractive distillation columns, resulting in simpler and cheaper separation of 1,3-butadiene from the mixed stream.

The catalyst is particularly useful for removing MAPD or acetylene in crude mixed $C_2$-$C_3$ olefin streams and phenyl acetylene in crude styrene stream by selective hydrogenation. Methyl acetylene/propadiene (MAPD) is not a compound but covers the unstable compounds methyl acetylene and propadiene which may be depicted as follows:

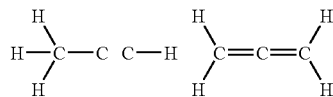

The improvement is made by depositing Ni promoted with palladium and preferably copper on a support. The catalyst may contain one or more optional elements from Group I and Group II, such as Ag, Ca, Mg, etc. When silver is used as an optional component, silver is deposited on a support in any of following methods; prior-deposition or post-deposition to deposition of nickel, co-deposition with nickel, combinations of two or all of these. The optional components, other than Ag are deposited on alumina prior to deposition of active metal components Ni, Cu, Pd and Ag. Deposition of Ni on a support can be carried out by performing either a single or multiple impregnations in any method.

A preferred catalyst is a supported catalyst for selective hydrogenation of acetylenes selected from the group consisting of 3-15 wt. % Ni, 0.005-0.2 Pd, 0.0-1 wt. % copper, 0.0-10 wt. % Ag, 0-1.5 of at least one member of Group IA and 0.0-25 wt. % of at least one member of Group IIA and IIB deposited on a support, more preferably selected from the group consisting of 4-11 wt. % Ni, 0.01-0.1 Pd, 0.01-0.6 wt. % copper, 0.0-5 wt. % Ag, 0.0-1.5 of at least one member of Group IA and 0.1-5 wt. % of at least one member of Group IIA and IIB deposited on a support.

The preferred support will have BET surface area from about 10 to 100 $m^2/g$, preferably from about 12 to 75 $m^2/g$. Examples of such supports are alumina, silica, beta-silicon carbide, carbon, mixed metal oxides, ceramics, various structured materials for column packing, etc. The preferred alumina is prepared by calcining at a temperature from about 1000 to 1250° C. The diameter of a preferred shaped support is from 0.2 mm to 3 mm, preferably from 0.4 to 2.5 mm, most preferably from 0.7 mm to 1.5 mm. The preferred alumina is alpha, theta, delta-alumina or a mixture of these, which have BET surface area, preferably from 10 to about 75 $m^2/g$. Additional optional elements are any elements from Group I and II in the Periodic Table.

A preferred support is aluminum oxide, which contains mixed oxides of $MAl_2O_4$ with spinel structures, where M is any divalent cation, such as Mg, Ca, Zn, Ni, Co, Cu, Mn, etc. Also, up to 30% of aluminum in mixed oxides can be replaced with Ga or In. The content of spinel in aluminum oxide support can be any amount, but preferably from 0.1% to 50%, most preferably from 0.2% to 20%.

When catalyst containing optional elements are prepared with alumina support, one or more elements from Group II is deposited on preferably gamma or eta-alumina and then calcined at from about 900 to 1250° C. to prepare a spinel containing alumina support. One can also prepare other divalent ions such as copper, nickel or copper-nickel spinel containing alumina support in a similar manner.

The selective hydrogenation can be carried out in any physical device in the presence of one or two catalysts, which have different compositions within this invention or are a combination of catalysts in this invention and other Ni-based catalysts or palladium-based catalysts. Examples of such devices are fixed bed reactors, catalytic distillation reactors, boiling point reactors, extractive distillation reactors, divided wall distillation reactors, moving bed reactors, stirred tank reactors, and trickle bed reactors. A combination of two or three of these physical devices can be used for multi-step selective hydrogenation. For example, the crude feed stream may be partially hydrogenated to remove acetylenic compounds in a catalytic distillation column reactor or extractive distillation column reactor as first reaction zone. The reaction product stream from the first reaction zone may be further hydrogenated to remove remaining acetylenic compounds in a fixed bed reactor as a second reaction zone.

In general, the catalyst deactivates slowly while in service. Partially deactivated catalyst is treated by washing with a solvent from about 170 to 600° F., preferably from 200 to 400° F. in the presence or absence of hydrogen to recover the catalyst activity. The examples of the suitable solvent for the catalyst washing are ethers, hydrocarbons, organic carbonates and ketones such as diethyl ether, tetrahydrofuran, furfural, gamma-butyrolactone, dimethyl carbonate, ethylene carbonate, alkyl nitriles, amides, methylpyrrolidinone, formylmorpholine, benzene, toluene, cyclohexane, ethylene glycol dimethyl ether, diethylene glycol dimethyl ether, dioxane, etc.

For the fixed bed operation, a solvent is fed to the reactor together with a hydrocarbon feed stream and hydrogen. Optionally a solvent is occasionally co-fed to the reactor with hydrocarbon feed. The solvent is recovered from the reactor effluent stream for the recycle. Still another option is, after interrupting the hydrocarbon feed, washing the catalyst with a solvent at temperature from about 100 to 450° F. and under a pressure from ambient to about 350 psig preferentially in the presence of a small amount of or in the absence of hydrogen depending on the washing temperature and the nature of the chosen solvent. Optionally the washed catalyst may be subjected to a post-washing thermal treatment at a temperature from about 170 to about 800° F. in a flow of hydrogen gas under a pressure from ambient to about 350 psig.

For the extractive or catalytic distillation operation for the selective hydrogenation, a solvent is introduced into the column either at a position above the catalyst bed or a position in the middle of the catalytic reaction zone with no reflux or minimum reflux of the overhead product stream. The solvent is recovered from the bottom stream or by sidedraw from the lower section of the column for recycle. The catalyst washing with solvent can be either continuous or occasional.

The evaluation of the catalyst performance is carried out by comparing recovery of a desired product for a given feedstock at a given conversion of acetylenic compounds or at the conversion required to meet specific product qualifications. For example, when acetylenic compounds in a crude mixed $C_3$ olefin feed stream are selectively hydrogenated, propylene is the desired product to be recovered from the product stream. The following mathematical formula defines the recovery of propylene.

Propylene recovery(%)=$N_P \times 100/N_F$ $N_F$=moles of propylene in feed stream, $N_P$=moles of propylene in product stream Since MAPD can be converted to propylene by selective hydrogenation, the recovery of propylene can be larger than 100 mole %.

Selectivity of MAPD is defined by the following formula.

Selectivity=$(N_P-N_F) \times 100/(M_F-M_P)$ where $M_P$=mole of MAPD in product stream, $M_F$=mole of MAPD in feed stream. It should be noted that the selectivity of MAPD decreases with the conversion of MAPD due to over-hydrogenation of propylene to propane.

Control Example 1

Conventional Pd-Based Catalyst

A commercial eggshell type Pd catalyst supported on alpha-alumina (2.5 mm spheres) was used to remove MAPD in a mixed $C_3$ stream by selective hydrogenation. 40 grams of the catalyst were loaded in a vertically mounted up-flow stainless steel fixed bed reactor (1 inch diameter×20 inches long). Two thermocouples at each end of the catalyst zone are installed to control the reactor temperature. The catalyst was activated at 220° F. by passing hydrogen at 350 cc per minutes for 2 hours. The selective hydrogenation of MAPD impurities in a $C_3$ feed stream was carried out at a fixed flow rate of 4.5 ml/min and hydrogen flow rate of from 20 to 110 sccm/min under 380 psig total reactor pressure. The feed comprised of 2.01 wt. % propyne, 0.57 wt. % propadiene, 95.19 wt. % propylene, etc. Because of exothermic heat of hydrogenation, the temperature at the end of the catalyst bed was higher than at the beginning of the catalyst bed. The temperatures of the hydrogenation were 120 to 135° F. at the end of the catalyst bed and about 80° F. at the beginning of the catalyst bed. The test result is listed in Table 1. The average MAPD content in the product at the highest MAPD conversion was 8 wt.ppm propyne with 43.8 mole % of the average selectivity of MAPD to propylene.

Control Example 2

Conventional Pd Catalyst

Another commercial eggshell type catalyst (0.3 wt. %) supported on alpha-alumina (3×3 mm pellets) was used to remove MAPD in the same feed used in the Control Example 1 by selective hydrogenation. 40 grams of the catalyst were loaded in the same reactor used in the Control Example 1. The catalyst was activated in an identical manner to the Control Example 1. The selective hydrogenation of MAPD impurities in the same feed used in the Control Example 1 was carried out at a constant flow rate of 4.5 ml/min and hydrogen flow rate of from 60 to 111 sccm/min under 380 psig total reactor pressure. The temperatures of the hydrogenation were about 135° F. at the end of the catalyst bed and 68-70° F. at the beginning of the catalyst bed. The test result is listed in Table 1. The performance of the catalyst was inferior to the palladium catalyst in the Control Example 1. The average MAPD content in the product at the highest MAPD conversion was 57 wt.ppm MAPD with 34.7 mole % of the average selectivity of MAPD to propylene.

Control Example 3

Non-Invention Ni-Based Catalyst

A Ni catalyst supported on a transition alumina was prepared. A gamma alumina trilope extrudate (1.3 mm diameter) was calcined at about 1000° C. for 3 hours in air. A solution of nickel nitrate was prepared by dissolving 183.6 g Ni(NO$_3$)$_2$.6H$_2$O in 300 g water. 300 grams of the calcined alumina support were placed in a rotary impregnator and then the nickel nitrate solution was poured on tumbling alumina extrudate support in the rotary impregnator. After 15 minutes cold roll, the contents in the rotary impregnator were dried at about 200° C. by blowing hot air into the rotary dryer. The dried product was calcined at 380° C. for 2 hours. Based on the amount of nickel nitrate used to prepare this catalyst, the finished catalyst would have 11 wt. % Ni on alumina support. Measurement of the physical properties of the finished catalyst indicated 133 m$^2$/g BET surface area, a total nitrogen adsorption pore volume of 0.669 cc/g and an average pore diameter of 18.6 nm.

40 grams of the catalyst were loaded in the same reactor used in the Control Example 1. The catalyst was activated at 250° F. in 300 sccm/min flow of a gas mixture of 33 vol % hydrogen in nitrogen for 1.5 hours and then for 3 hours at each 670 F and 770° F. by passing 350 cc per min of pure hydrogen gas. The selective hydrogenation of MAPD impurities in the same feed used in the Control Example 1 was carried out at a constant flow rate of 4.5 ml/min and hydrogen flow rate of from 20 to 95 sccm/min under 380 psig total reactor pressure. The temperatures of the hydrogenation were 120 to 123° F. at the end of the catalyst bed and from 75° to 85° F. at the beginning of the catalyst bed. The test result is listed in Table 1. This nickel catalyst shows a remarkable performance compared with the catalysts in the Control Examples 1 and 2. The conversion of MAPD was 100%. The selectivity of MAPD to propylene was 48.3 m %.

Example 4

Invention

This example demonstrates the preparation technique of a nickel-based catalyst promoted with copper and palladium supported on a nickel spinel containing alumina support. A double impregnation technique was used.

The gamma-alumina (1.3 mm diameter trilope extrudate) support used in the Control Example 3 was calcined at 1100° C. in air for 3 hours. The calcined alumina had 96.6 m²/g BET surface area, a total nitrogen adsorption pore volume of 0.622 cc/g and an average pore diameter of 27.7 nm. However, this calcined alumina was not used to prepare the nickel catalyst. To prepare the nickel spinel containing alumina support, 1 wt. % nickel was deposited on gamma-alumina and then was calcined at 1100° C. for 3 hours in air. The spinel containing calcined alumina had 26 m²/g BET, a total nitrogen pore volume of 0.167 cc/g and an average pore diameter of 25.2 nm. This material was used to prepare a nickel-based catalyst as follows.

A mixed solution of nickel nitrate and copper nitrate was prepared by dissolving 106 g Ni(NO$_3$)$_2$.6H$_2$O and 4.5 g Cu(NO$_3$)$_2$.2.5H$_2$O in 300 g water. 300 grams of the calcined nickel spinel containing alumina support were placed in a rotary impregnator and then the mixed solution was poured on tumbling extrudate support in the rotary impregnator. After 15 minutes cold roll, the content in a rotary impregnator was dried at about 200° C. by blowing hot air into the rotary impregnator. The dried product was calcined at 350° C. for 2 hours. Another mixed solution of nickel nitrate, copper nitrate and palladium nitrate was prepared by dissolving 60 g Ni(NO$_3$)$_2$.6H$_2$O, 2.54 g Cu(NO$_3$)$_2$.2.5H$_2$O and 0.74 g Pd(NO$_3$)$_2$.xH$_2$O (42.8% Pd) in 300 grams of water. A second impregnation was performed with this mixed solution on the first impregnation product in similar manner to the first impregnation. The impregnation product was calcined at 380° C. for 2 hours. Based on the amounts of materials used in two impregnations to prepare this catalyst, the finished catalyst would have 9.98 wt. % Ni, 0.57 wt. % Cu and 0.094 wt % Pd.

40 grams of this catalyst were loaded in the same reactor used in the Control Example 1. The catalyst was activated in an identical manner to the Example 4. The selective hydrogenation of MAPD impurities in the same feed used in the Control Example 1 was carried out at a given constant hydrocarbon feed flow rate of 4.5 ml/min and hydrogen flow rate of from 20 to 95 sccm/min under 380 psig total reactor pressure. The temperatures of the hydrogenation were from 119 to 121° F. at the end of the catalyst bed and from 75° to 83° F. at the beginning of the catalyst bed. The test result is listed in Table 1. The conversion of MAPD was 100% with 76.4 m % selectivity of MAPD to propylene.

Example 5

Invention

This example demonstrates the preparation technique of a nickel-based catalyst promoted with copper and palladium supported on a nickel spinel containing alumina support. Double impregnation technique was used.

To prepare the nickel spinel containing alumina support, 1 wt. % nickel was deposited on the gamma-alumina used in the Control Example 3 and then was calcined at 1125° C. for 3 hours in air. The physical properties of the spinel containing calcined alumina were 24.4 m²/g BET, a total nitrogen adsorption pore volume of 0.145 cc/g and an average pore diameter of 23.7 nm. This material was used to prepare a nickel-based catalyst. A mixed solution of nickel nitrate and copper nitrate was prepared by dissolving 127.2 g Ni(NO$_3$)$_2$.6H$_2$O and 5.41 g Cu(NO$_3$)$_2$.2.5H$_2$O in 300 grams of water. 300 grams of the calcined nickel spinel containing alumina support were placed in a rotary impregnator and then the mixed solution was poured on tumbling alumina extrudate support in the rotary impregnator. After 15 minutes cold roll, the content in the rotary impregnator was dried at about 200° C. by blowing hot air into the rotary impregnator. The dried product was calcined at 350° C. for 2 hours. Another mixed solution of nickel nitrate, copper nitrate and palladium nitrate was prepared by dissolving 38.8 g Ni(NO$_3$)$_2$.6H$_2$O, 1.63 g Cu(NO$_3$)$_2$.2.5H$_2$O and 0.44 g Pd(NO$_3$)$_2$.xH$_2$O (42.8% Pd) in 300 g water. A second impregnation was performed with this mixed solution on the first impregnation product in similar manner to the first impregnation. The impregnation product was calcined at 380° C. for 2 hours. Based on the amounts of materials used in two impregnations to prepare this catalyst, the finished catalyst would have 9.99 wt. % Ni, 0.57 wt. % Cu and 0.056 wt % Pd.

50 grams of this catalyst were loaded in the same reactor used in the Control Example 1. The catalyst was activated in an identical manner to the Example 4. The selective hydrogenation of MAPD impurities in the same feed used in the Control Example 1 was carried out at a given constant hydrocarbon feed flow rate of 4.5 ml/min and hydrogen flow rate of from 30 to 105 sccm/min under 380 psig total reactor pressure. The temperatures of the hydrogenation were from about 119 to about 129° F. at the end of the catalyst bed and from about 77 to about 81° F. at the beginning of the catalyst bed. The test result is listed in Table 1. The performance of this catalyst was superior to the catalysts in the Control Examples 1, 2 and 3. The conversion of MAPD was 100% with 64.8 m % of the selectivity of MAPD to propylene.

Example 6

Invention

This example demonstrates the preparation technique of a nickel-based catalyst promoted with copper and palladium supported on a nickel spinel containing alumina support. A single impregnation was performed.

To prepare the nickel spinel containing alumina support, 1 wt. % nickel was deposited on the gamma-alumina used in the Control Example 3 and then was calcined at 1150° C. for 3 hours in air. The spinel containing calcined alumina had 16.8 m²/g BET, a total nitrogen adsorption pore volume of 0.09 cc/g and an average pore diameter of 21.1 nm. XRD indicates about 95% alpha-alumina, about 5% delta and trace theta. This material was used to prepare a nickel catalyst as follows. A mixed solution of nickel nitrate, copper nitrate and palladium nitrate was prepared by dissolving 166 g Ni(NO$_3$)$_2$.6H$_2$O, 7.04 g Cu(NO$_3$)$_2$.2.5H$_2$O and 0.74 g Pd(NO$_3$)$_2$.xH$_2$O (42.8% Pd) in 305 g water. 300 grams of the calcined nickel spinel containing alumina support were placed in a rotary impregnator, and then the mixed solution was poured on tumbling alumina extrudate support in a rotary impregnator. After 15 minutes cold roll, the content in the rotary impregnator was dried at about 200° C. by blowing hot air into the rotary impregnator. The dried product was calcined at 370° C. for 2 hours. Based on the amounts of materials used in two impregnations to prepare this catalyst, the finished catalyst would have 9.98 wt. % Ni, 0.57 wt. % Cu and 0.094 wt % Pd. The finished catalyst had 9.4 m²/g BET, a total nitrogen adsorption pore volume of 0.035 cc/g and an average pore diameter of 14.8 nm. The analysis of the catalyst indicates the following composition; 10.4 wt. % Ni, 0.55 wt. % Cu and 0.074 wt. % Pd.

40 grams of this catalyst were loaded in the same reactor used in the Control Example 1. The catalyst was activated in an identical manner to the Example 4. The selective hydrogenation of MAPD impurities in the same feed used in the Control Example 1 was carried out at a given constant hydrocarbon feed flow rate of 4.5 ml/min and hydrogen flow rate of from 20 to 105 sccm/min under 380 psig total reactor pressure. The temperatures of the hydrogenation were from 118 to 133° F. at the end of the catalyst bed and from 70° to 80° F. at the beginning of the catalyst bed. The test result is listed in Table 1. The performance of this catalyst was superior to the catalysts in the Control Examples 1, 2 and 3. The average MAPD content in the product at the highest MAPD conversion was 5 wt. ppm propylene with 53.6 mole % of the average selectivity of MAPD to propylene.

Example 7

Invention

This example demonstrates the preparation technique of a nickel-based catalyst promoted with copper and palladium supported on magnesium-spine alumina.

A spherical gamma-alumina (1.64 mm spheres), whose physical properties are 145 m²/g BET surface area, 0.925 cc/g total nitrogen pore volume and 21.6 nm average pore diameter, was used to prepare magnesium-spinel alumina. A magnesium nitrate solution was prepared by dissolving 6 grams of Mg(NO3)2.6H2O in 320 grams water. 300 grams of gamma-alumina were impregnated with this magnesium nitrate solution. After drying the impregnated alumina at about 200 C for 2 hours, the dried product was calcined at 1100 C for 3 hours and then at 1150 C for 2 hours in air to prepare the magnesium-spinel/alumina support. The support had 60.4 m²/g BET surface area, a total nitrogen pore volume of 0.548 cc/g and an average pore diameter of 37.3 nm.

A mixed solution of nickel nitrate and copper nitrate was prepared by dissolving 9681 grams of Ni(NO3)2.6H2O and 4.11 grams of Cu(NO3)2.2.5H2O in 300 grams of water. 274 grams of the magnesium-spinel/alumina were placed in a rotary impregnator and then the mixed solution was poured on the support. After 10 minutes cold rolling, the content in the impregnator was dried at about 200 C by blowing hot air into the rotary impregnator. The dried product was calcined at 350 C for two hours. Another mixed solution of nickel nitrate, copper nitrate and palladium nitrate was prepared by dissolving 54.8 grams of Ni(NO$_3$)$_2$.6H$_2$O, 2.32 grams of Cu(NO$_3$)$_2$.2.5H$_2$O and 0.66 grams of Pd(NO$_3$)$_2$.xH$_2$O (42.8 wt % Pd) in 300 grams of water. Second impregnation of the first impregnation product with the second mixed solution was performed in similar manner. The dried impregnation product was calcined at 380 C for 2 hours. Based on materials used to prepare this catalyst, the active metal compositions on the support are 9.96 wt % Ni, 0.57 wt % Cu and 0.09 wt % Pd. The finished catalyst had 59.3 M/g BET surface area, a total nitrogen pore volume of 0.457 cc/g and an average pore diameter of 31.8 nm.

40 grams of this catalyst were loaded in the same reactor used in the Control Example 1. The catalyst was activated in identical manner to the Control Example 3. The selective hydrogenation of MAPD impurities in the same feed used in the Control Example 1 was carried out at a given constant hydrocarbon feed flow rate of 4.5 ml/min and hydrogen flow rate of from 50 to 80 sccm/min under 380 psig total reactor pressure. The temperatures of the hydrogenation were from 120 to 125 F at the end of the catalyst bed and from 88 to 92 F at the beginning of the catalyst bed. The test result is listed in Table 1. The performance of this catalyst was superior to the catalysts in the Control Examples 1, 2 and 3. The conversion of MAPD was 100% with 62.8 in % of the selectivity of MAPD to propylene.

TABLE 1

| | $H_2$ rate | Product | | Recovery of | Selectivity[†] |
|---|---|---|---|---|---|
| | Sccm/min | MAPD* | PA* | $C_3H_6$ (m %) | (m %) |
| Control Example 1 | 110 | 8 | 8 | 101.2 | 43.8 |
| Control Example 2 | 110 | 57 | 26 | 101.0 | 34.7 |
| Control Example 3 | 70 | 0 | 0 | 101.4 | 48.3 |
| Example 4 | 67 | 0 | 0 | 102.2 | 76.4 |
| Example 5 | 70 | 0 | 0 | 101.8 | 64.8 |
| Example 6 | 105 | 5 | 5 | 101.5 | 53.6 |
| Example 7 | 59 | 0 | 0 | 101.8 | 62.8 |

*wt. ppm
[†]based on conversion of MAPD to propylene

The invention claimed is:

1. A process of selectively hydrogenating acetylenic compounds comprising contacting said acetylenic compounds with a hydrogenation catalyst comprising Ni with a promoting amount of Pd deposited on an aluminum oxide support, which contains mixed oxides of $MAl_2O_4$ with spinel structures, where M is selected from the group consisting of Co, Ni, Ca, and Zn, in the presence of hydrogen under conditions of temperature and pressure to at least partially hydrogenate said acetylenic compounds to the corresponding compounds having less unsaturation than said acetylenic compounds.

2. The process according to claim 1, wherein the support has BET surface area from about 10 to 100 m²/g.

3. The process according to claim 2, wherein the support has BET surface area from about 12 to 75 m²/g.

4. The process according to claim 1, wherein the support comprises alumina prepared by calcining at a temperature from about 1000 to 1250° C.

5. The process according to claim 4, wherein the support comprises gamma or eta-alumina.

6. The process according to claim 1, the catalyst comprising 3-15 wt. % Ni promoted with 0.005-0.2 wt. % Pd.

7. The process according to claim 6, wherein the support has BET surface area from about 10 to 100 m²/g.

8. The process according to claim 7, wherein the support has BET surface area from about 12 to 75 m²/g.

9. The process according to claim 6, wherein the support comprises alumina prepared by calcining at a temperature from about 1000 to 1250° C.

10. The process according to claim 9, wherein the support comprises gamma or eta-alumina.

11. The process according to claim 1, the catalyst further comprising at least one component selected from the group consisting of 0.0-1 wt. % copper, 0.0-10 wt. % Ag, 0-1.5 wt. % of at least one member of Group IA, and 0.0-25 wt. % of at least one member of Group IIA and IIB.

12. The process according to claim 11, wherein the support has BET surface area from about 10 to 100 m²/g.

13. The process according to claim 12, wherein the support has BET surface area from about 12 to 75 m²/g.

14. The process according to claim 11, wherein the support comprises alumina prepared by calcining at a temperature from about 1000 to 1250° C.

15. The process according to claim 14, wherein the support comprises gamma or eta-alumina.

16. The process according to claim 11, wherein the catalyst comprises 4-11 wt. % Ni promoted with 0.01-0.1 Pd wt. %, the catalyst further comprising at least one component selected from the group consisting of 0.01-0.6 wt. % copper, 0.0-5 wt. % Ag, 0.0-1.5 wt. % of at least one member of Group IA, and 0.1-5 wt. % of at least one member of Group IIA and IIB.

17. The process according to claim 16, wherein the support has BET surface area from about 10 to 100 m²/g.

18. The process according to claim 17, wherein the support has BET surface area from about 12 to 75 m²/g.

19. The process according to claim 16, wherein the support comprises alumina prepared by calcining at a temperature from about 1000 to 1250° C.

20. The process according to claim 19, wherein the support comprises gamma or eta-alumina.

* * * * *